United States Patent
Gmur et al.

(10) Patent No.: US 7,030,204 B2
(45) Date of Patent: Apr. 18, 2006

(54) NOVOLAK CYANATE-BASED PREPOLYMER COMPOSITIONS

(75) Inventors: Martin Gmur, Unterageri (CH); Ulrich Daum, Hofstetten (CH); Brigitta Heyl-Frank, Visp (CH); Paul Hanselmann, Glis (CH); Alessandro Falchetto, Domodossola (IT)

(73) Assignee: Lonza AG, Basel (CH)

( * ) Notice: Subject to any disclaimer, the term of this patent is extended or adjusted under 35 U.S.C. 154(b) by 257 days.

(21) Appl. No.: 10/467,380

(22) PCT Filed: Feb. 5, 2002

(86) PCT No.: PCT/EP02/01154

§ 371 (c)(1),
(2), (4) Date: Aug. 7, 2003

(87) PCT Pub. No.: WO02/064548

PCT Pub. Date: Aug. 22, 2002

(65) Prior Publication Data

US 2004/0097690 A1 May 20, 2004

Related U.S. Application Data

(60) Provisional application No. 60/331,300, filed on Nov. 14, 2001.

(30) Foreign Application Priority Data

Apr. 24, 2002 (EP) .............................. 01103068

(51) Int. Cl.
C08G 18/00 (2006.01)
C08G 18/08 (2006.01)

(52) U.S. Cl. .................. 528/44; 528/162; 524/858; 524/871; 524/873

(58) Field of Classification Search ............. 528/44, 528/162; 524/858, 871, 873
See application file for complete search history.

(56) References Cited

U.S. PATENT DOCUMENTS 4,094,852 A 6/1978 Sundermann et al.
4,713,442 A 12/1987 Woo et al.

OTHER PUBLICATIONS

Sase et al; Modified cyante ester–based polymer films with—their maunfacture; May 1999; Chem Abstract 130: 353426.*
Mizuno et al; Cyanate resin varnishes for printed circuit boards—metal–clad laminates; Oct. 1998; Chem Abstract 129: 331912.*
Mizuno et al; Cyanate resin compositions—metal–clad laminates; Oct. 1998; Chem Abstract 129: 331911.*
Tsunemi et al; Preparation of—printed circuit laminates; Jun. 1993; Chem Abstract 120; 324905.*
A copy of the International Search Report from Applicant's International Applicaiton.

* cited by examiner

*Primary Examiner*—Duc Truong
(74) *Attorney, Agent, or Firm*—Fisher, Christen & Sabol

(57) ABSTRACT

Described are prepolymer compositions on the basis of novolak cyanates of the general formula

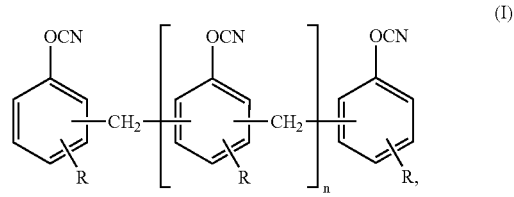

(I)

wherein n is a number from 0 to 20 and the radicals R are identical or different and represent hydrogen or methyl. The compositions contain: 30 to 90 parts by weight of a prepolymer from novolak cyanates (I) wherein R=hydrogen (Ia) and 10 to 70 parts by weight of novolak cyanates (I) wherein R=methyl (Ib), and optionally highly disperse silicon dioxides and/or particulate or fibrous fillers. The inventive compositions are solid at normal temperature and can be ground to flowable powders. They have excellent stability when stored and are easy to process and especially suitable for use as the resin component in base materials for printed circuits on resin-bound abrasive products.

16 Claims, No Drawings

NOVOLAK CYANATE-BASED PREPOLYMER COMPOSITIONS

This is a 371 U.S. national stage application of International (PCT) Patent Application PCT/EP02/01154, filed on Feb. 5, 2002, that has priority benefit of U.S. Provisional Application Ser. No.60/331,300, filed on Nov. 14, 2001, and that has priority benefit of European Patent Application No. 01103068.1, filed on Feb. 9, 2001.

The invention relates to prepolymer compositions based on novolak cyanates.

Novolak cyanates are reactive oligomeric compounds of the general formula

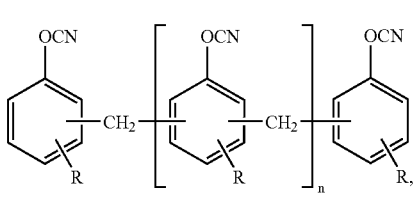

(I)

in which n is generally a number from 0 to 20 and the radicals R are identical or different and represent hydrogen or methyl. The bonds to the methylene groups which link the benzene rings can in principle go out to the cyanate groups from the ortho-(o), meta-(m) or para-(p) positions and the radicals R can be located in any of the remaining positions. Linking preferably takes place through the ortho and para positions. The compounds are customarily in the form both of oligomer mixtures (with different values of n) and of isomer mixtures (with different linkage patterns, preferably o or p for the terminal benzene rings and o,o or o,p for the nonterminal benzene rings) and are obtainable from the condensation products of phenol or cresols with formaldehyde by reaction with cyanogen chloride or bromide. The oligomer mixtures are customarily characterized by stating the average value of n. This average value—unlike the value of n in one individual molecule—can also be nonintegral.

Novolak cyanates (I) with R=hydrogen or R=methyl are available commercially, for example, under the designation Primaset® from the company Lonza AG, Basle, Switzerland.

The novolak cyanates can be polymerized thermally, optionally in the presence of catalysts, to form polytriazines, with three cyanate groups in each case undergoing cyclotrimerization to form a 1,3,5-triazine ring. This cyclotrimerization is strongly exothermic. Owing to the outstanding thermal, mechanical, and electrical properties of polytriazines, novolak cyanates are being used to an increasing extent, alone or in a mixture with other cyanates, for producing high-temperature-resistant moldings.

In order to improve the processing properties and to lower the exothermic heat in the course of curing, it is advantageous for certain applications to carry out the cyclotrimerization in part even before the shaping operation, to give a—preferably solid—"prepolymer", which still has free cyanate groups, optionally is soluble in organic solvents, and after the shaping operation can be cured to completion and crosslinked with reaction of the remaining cyanate groups. The prepolymers from the prior art, however, also have negative properties, in that they are tacky and are neither readily grindable nor free-flowing or, owing to excessive crosslinking, are no longer shapeable or do not have the desired reactivity.

An object of the present invention was therefore to provide novolak cyanate prepolymers which are solid at standard temperature and meltable at a higher temperature, can easily be ground to a readily free-flowing powder, and are neither too reactive nor too inert. In particular they should be storable for a long time at standard temperature, should have a gel time of at least 6 minutes at 200° C., but after gel formation should quickly cure fully.

In accordance with the invention this object is achieved by the prepolymer compositions of the invention.

It has been found that defined mixtures of prepolymerized and nonprepolymerized novolak cyanates, specifically mixtures of from 30 to 90 parts by weight of prepolymers of novolak cyanates of the general formula

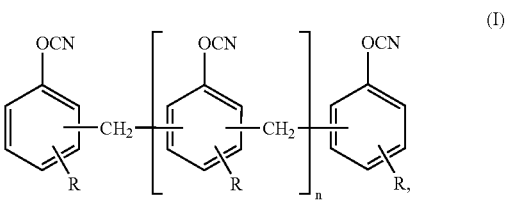

(I)

in which n is a number from 0 to 20 and the radicals R represent hydrogen (Ia), with from 10 to 70 parts by weight of novolak cyanates (I) in which R in each case represents methyl (Ib), have the desired properties. The sum of the parts by weight of prepolymer and novolak cyanate (Ib) in this composition amounts in each case to 100.

The compositions of the invention preferably contain from 50 to 70 parts by weight of prepolymers of novolak cyanates (Ia) and from 30 to 50 parts by weight of novolak cyanates (Ib).

The average value of n in the novolak cyanate (Ia) from which the prepolymer has been obtained is preferably a number from 0 to 5.

Particularly good results are achieved in this context with prepolymers having a refractive index $n_D^{98}$ (refractive index for the Na D-line at 98° C.) of at least 1.58, preferably at least 1.582.

Likewise preferred are prepolymer compositions in which the average value of n in the novolak cyanates (Ib) is from 1 to 10.

In one preferred embodiment the prepolymer compositions of the invention further contain up to 5% by weight of a highly disperse silica. As highly disperse silica it is possible to use both pyrogenic (e.g., Aerosil®) and precipitated (e.g., Sipernat®) products. Particular preference is given to pyrogenic silicas.

The prepolymer compositions of the invention are suitable in particular as a resin component in base materials for printed circuit boards or syntheticresin-bound abrasive products.

The examples which follow illustrate the execution of the invention without representing any restriction.

The gel times were determined at 200±1° C. in analogy to DIN 16 945 using Gelnorm® instruments (Gel Instrumente AG, CH-8800 Thalwil) on samples of approximately 12 g in conventional test tubes (16×160 mm). The duration of one up-down cycle was 10 s. The refractive indices were determined using an Abbe refractometer thermostated at 98° C.

The grinding experiments were conducted in a vibratory mill with ceramic grinding beads and grinding drums. The starting materials used were Primaset® PT-30 (Ia, n≈3), a yellow resin of high viscosity with $n_D^{98}$=1.5667 and a gel time of 2.5 h, and Primaset® CT-90 (Ib, n=1–10), a yellow amorphous powder having a gel time of 0.5 h. Both products are available from Lonza AG, Basle, Switzerland.

COMPARATIVE EXAMPLE 1

Prepolymers from Primaset® PT-30

Primaset® PT-30 was heated at 120° C. for 30–40 min for liquefaction and in portions each of 10–20 g was poured into disposable aluminum trays (Ø=60 mm). The prepolymerization was conducted at 165° C. for times of 1–9 h. The key properties of the samples thus obtained are collated in table 1 below.

It was found that with Primaset® PT-30 alone the desired properties cannot be achieved: either the prepolymer is ungrindable or sticks together or it has already undergone crosslinking to such an extent that further processing is no longer possible.

EXAMPLE 1

Inventive

The procedure described in comparative example 1 was initially repeated but after the polymerization at 165° C. the samples were cooled to 120° C. and at this temperature were mixed with Primaset® CT-90 so as to form in each case a liquid homogeneous mixture. The refractive index of these mixtures and, after cooling to standard temperature, their grindability were determined. A measurement was made of the gel time as well. Good results were obtained with prepolymerization times of 6¼ and 6½ h. The key results are collated in table 2 below.

TABLE 1

| t [h] | $n_D^{98}$ | Gel time [min] | Appearance [RT] | Appearance (165° C.) | Grindability | Free-flowability | Free-flowability after 3'/50° C. |
|---|---|---|---|---|---|---|---|
| 1 | 1.5696 | — | yl-rd, honeylike | highly mobile | — | — | — |
| 2 | 1.5714 | — | yl-rd, honeylike | highly mobile | — | — | — |
| 3 | 1.5738 | — | yl-rd, honeylike | highly mobile | — | — | — |
| 4 | 1.5744 | — | or-bn, flows | highly mobile | — | — | — |
| 5 | 1.5780 | — | or-bn, flows | highly mobile | — | — | — |
| 5½ | 1.5809 | 24 | or-bn, solid, plastic | highly mobile | — | — | — |
| 6 | 1.5810 | 19 | or-bn, solid, plastic | liquid | — | — | — |
| 6½ | 1.5846 | 14 | or-bn, solid, plastic | liquid | poor (triturated with dry ice) | none | completely melted |
| 7 | 1.588* | 7 | or-bn, solid | viscous | grindable | with tapping | sticks together |
| 7½ | not measurable | | or-bn, solid | viscous | readily grindable | good | sticks together |
| 8 | (cannot be liquefied) | | or-bn, solid | solid | readily grindable | good | good after tapping |
| 8½ | | | or-bn, solid | solid | readily grindable | good | good after tapping |
| 9 | | | or-bn, solid | solid | n.m. | n.m. | n.m. |

*nearly impossible to determine
yl = yellow;
or = orange;
rd = red;
bn = brown;
n.m. = not measured

COMPARATIVE EXAMPLE 2

Prepolymers From Mixtures of Primasete PT-30 and Primaset® CT-90 (Joint Prepolymerization)

The procedure described in comparative example 1 was repeated but using instead of Primaset® PT-30 alone mixtures of Primaset® PT-30 and Primaset® CT-90 in proportions of 90:10, 70:30, 50:50, 30:70, 20:80 and 10:90. The prepolymers obtainable in this way were again either not grindable or free-flowing or had already undergone excessive crosslinking.

TABLE 2

| Ib (parts by weight) | t [h] | Gel time [min] | Appearance (RT/165° C.) | Grindability at RT | Free-flowability at RT |
|---|---|---|---|---|---|
| 0*) | 6¼ | 14 | solid/sluggishly mobile | — | — |
| 10 | 6¼ | 12 | solid/sluggishly mobile | good | Good |
| 20 | 6¼ | 14 | solid/sluggishly | good | Good |

TABLE 2-continued

| Ib (parts by weight) | t [h] | Gel time [min] | Appearance (RT/165° C.) | Grindability at RT | Free-flowability at RT |
|---|---|---|---|---|---|
| 30 | 6¼ | 16 | solid/sluggishly mobile | good | Good |
| 50 | 6¼ | 14 | solid/sluggishly mobile | good | Good |
| 0*) | 6½ | 15 | solid/sluggishly mobile | — | — |
| 10 | 6½ | 16 | solid/sluggishly mobile | limited | poor, with tapping |
| 20 | 6½ | 18 | solid/sluggishly mobile | good | poor, with tapping |
| 30 | 6½ | 17 | solid/sluggishly mobile | good | Good |
| 50 | 6½ | 15 | solid/sluggishly mobile | good | Good |

*)not inventive

The samples exhibited the desired temperature behavior (solid at room temperature, sluggishly mobile at 165° C.) and an advantageous gel time. In contrast to the non-inventive samples (0 parts Primaset® CT-90), all were grindable and after grinding were free-flowing. By adding 1% of highly disperse silica (Aerosil® R972, Degussa-Hüls) it was possible to achieve a further significant improvement in free-flowability.

What is claimed is:

1. A prepolymer composition based on novolak cyanates of the formula:

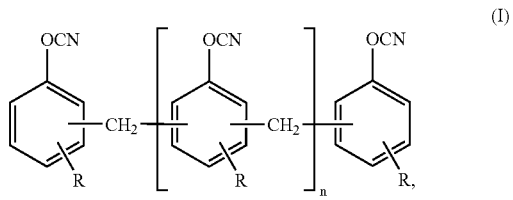

(I)

in which n is a number from 0 to 20 and the radicals R are identical or different and each is hydrogen or methyl, the prepolymer composition containing from 30 to 90 parts by weight of a prepolymer of the novolak cyanates (I) wherein R is hydrogen (Ia), and from 10 to 70 parts by weight of novolak cyanates (I) wherein with R is methyl (Ib).

2. The prepolymer composition of claim 1, wherein the average value of n in the prepolymer (Ia) is from 0 to 5.

3. The prepolymer composition of claim 2, wherein the prepolymer of the novolak cyanate (Ia) used has a refractive index $n_D^{98}$ of at least 1.58.

4. The prepolymer composition of claim 3, wherein the average value of n in the novolak cyanates (Ib) is from 1 to 10.

5. The prepolymer composition of claim 4, wherein the prepolymer composition further contains up to 5 percent by weight of a highly disperse silica.

6. The prepolymer composition of claim 5, wherein the highly disperse silica comprises a pyrogenic silica.

7. The prepolymer composition of claim 4, wherein the prepolymer composition further comprises at least one particulate and/or fibrous filler.

8. The process comprising utilizing the prepolymer composition of claim 1 as a resin component in base materials for printed circuit boards or synthetic resin-bound abrasive products.

9. The prepolymer composition of claim 1, wherein the prepolymer composition contains from 50 to 70 parts by weight of a prepolymer of the novolak cyanates (I) wherein R is hydrogen (Ia).

10. The prepolymer composition of claim 1, wherein the prepolymer composition contains from 30 to 50 parts by weight of the novolak cyanates (I) wherein R is methyl (Ib).

11. The prepolymer composition of claim 2, wherein the prepolymer of the novolak cyanate (Ia) used has a refractive index $n_D^{98}$ of at least 1.582.

12. The prepolymer composition of claim 1, wherein the average value of claim n in the novolak cyanates (Ib) is from 1 to 10.

13. The prepolymer composition of claim 1, wherein the prepolymer composition further contains up to 5 percent by weight of a highly disperse silica.

14. The prepolymer composition of claim 13, wherein the highly disperse silica comprises a pyrogenic silica.

15. The prepolymer composition of claim 1, wherein the prepolymer composition further comprises at least one particulate and/or fibrous filler.

16. The process comprising utilizing the prepolymer composition of claim 7 as a resin component in base materials for printed circuit boards or synthetic resin-bound abrasive products.

* * * * *